United States Patent [19]
Eggler et al.

[11] Patent Number: 6,123,545
[45] Date of Patent: Sep. 26, 2000

[54] MAINS-OPERATED DEVICE FOR CURING BY LIGHT A POLYMERIZABLE DENTAL MATERIAL

[75] Inventors: Andreas Eggler, Wolfurt, Austria; Gottfried Rohner, Altstätten, Switzerland

[73] Assignee: Ivoclar A.G., Schaan, Liechtenstein

[21] Appl. No.: 09/287,445

[22] Filed: Apr. 7, 1999

Related U.S. Application Data

[60] Provisional application No. 60/089,227, Jun. 15, 1998.

[30] Foreign Application Priority Data

Apr. 8, 1998 [DE] Germany ............ 198 15 846

[51] Int. Cl.[7] ............................................. A61C 3/00
[52] U.S. Cl. .................................................. 433/29
[58] Field of Search .......................... 433/29; 250/504 H

[56] References Cited

U.S. PATENT DOCUMENTS

| | | | |
|---|---|---|---|
| 4,298,806 | 11/1981 | Herold | 250/504 H |
| 4,385,344 | 5/1983 | Gonser | 250/504 H |
| 4,839,566 | 6/1989 | Herold | 31/308 |
| 4,876,482 | 10/1989 | Stadler | 313/579 |
| 5,146,134 | 9/1992 | Stadler | 313/579 |
| 5,184,044 | 2/1993 | Thomas | 313/638 |
| 5,803,729 | 9/1998 | Tsimerman | 433/29 |
| 5,879,159 | 3/1999 | Cipolla | 433/29 |
| 5,912,470 | 6/1999 | Eibofner et al. | 433/29 |

FOREIGN PATENT DOCUMENTS

| | | |
|---|---|---|
| 28 41 112 | 4/1980 | Germany . |
| 38 40 984 | 6/1990 | Germany . |

*Primary Examiner*—John J. Wilson
*Attorney, Agent, or Firm*—Alan S. Korman; John C. Thompson

[57] ABSTRACT

A mains-operated device for curing by light polymerizable dental material has a housing with a light guide and a cooling fan. A halogen light source, including a reflector and a spiral-wound filament, is positioned in the housing and emits light through the light guide. A control device is connected to the light source. The reflector is positioned at an end of the filament remote from the light guide. The reflector is transmissive for infrared radiation. The reflector is positioned in the cooling air flow of the fan. The control device supplies the filament with a voltage of 100 V to 240 V. The filament provides luminance of more than 750 cd.

16 Claims, 3 Drawing Sheets

MAINS-OPERATED DEVICE FOR CURING BY LIGHT A POLYMERIZABLE DENTAL MATERIAL

The application claims benefit of provisional application 60/089,227 Jun. 15, 1998.

BACKGROUND OF THE INVENTION

The present invention relates to a mains-operated device for curing by light polymerizable dental material wherein the device comprises a light source including a filament and a reflector which extends on a side of the filament remote from the dental material, wherein the reflector is transmissive for infrared radiation and is positioned in a cooling air flow of the cooling fan of the device.

Light-curing devices for dental applications are either in the form of mains-operated devices or battery-operated devices. While battery-operated light-curing devices have advantages with respect to their manipulation, especially when they are in the form of hand-held apparatus, since operation without an attached cable is possible, mains-operated light-curing devices have the advantage that they are independent of the securing means of the battery or accumulator, do not require recharging and operating time monitoring while, at the same time, their luminance is uniform, i.e., independent of the charge state of the accumulator, and furthermore, the luminance is much greater.

Light sources for mains-operated light-curing devices are usually in the form of conventional low voltage cinema projection lamps having either a reflector attached to the housing or an integrated reflector as known from German Offenlegungsschrift 28 41 112. Due to the considerable heating of such a lamp it must be cooled intensively which requires a correspondingly powerful fan. The cooling air flow of the fan is designed such that it will not impact the treatment area of the device. However, the cooling air stream exiting at the rearward end will bother the dentist using the device when the light curing device is a hand-held apparatus.

When employing a mains-operated light-curing device, a transformer must be used which is usually provided in a separate base station whereby the supply cable for the hand-held apparatus extends between the hand-held apparatus and the base station. Especially for high output devices, the transformer thus emits a correspondingly strong electromagnetic field which is undesirable in dental practices because other sensitive devices with sensors can be impeded in their operation and diagnostic results of these devices can be negatively affected. Accordingly, for correspondingly strong transformers an insulation of the housing of the supply station is desirable which, however, would impede proper cooling and is therefore not realized in practice. It is suggested to separate the supply station especially from the hand-held apparatus and separately from other diagnostic tools which, however, requires a correspondingly long supply cable which is in turn undesirable with respect to manipulation of the device.

Therefore, it has been suggested to replace the conventional transformers with a power pack. They allow reduction of the weight of the supply station, but emit radiation of a higher frequency which must then be shielded in order to avoid operational malfunction of other devices. Also, such power packs require a plurality of electronic components and their manufacture is complicated because an adaptation to selected specifications is required.

A disadvantage of light-curing devices of the prior art, when operated by mains, is that the employed transformer is costly. The presence of the base station also, in general, impedes the operation of a dental practice since such a base station is an additional device which is required but can be viewed as an auxiliary device for the pistol-shaped light-curing device.

The light-curing devices, especially when they are hand-held apparatus, advantageously employ a so-called soft start. The electrical power supplied to the light source is slowly increased, for example, over a time period of 4 seconds, in order to prevent that a patient would be accidentally blinded when abruptly the full output of the light source would be released. The soft start allows the patient to close his eyes or to turn his head.

In addition to the transformer, a corresponding electronic is required in the supply station which requires rectification and smoothing of the alternate current supplied by the transformer and thus further increases the control expenditure. Also, in the known light-curing devices with soft start the output electronic must be provided within the supply station. In high-quality light-curing devices the detection of the emitted light output is required at the hand-held apparatus which requires a control circuit extending through the supply cable.

Dental material to be cured by light polymerization must be completely hardened during the polymerization cycle in order to prevent that the filling remains somewhat soft, thus causing gap formation at the edges which could result in secondary tooth decay.

Due to their excellent manipulation properties, dentists prefer polymerizable dental materials even for complex fillings with a respective great filling depth. For such fillings, the risk of incomplete polymerization of the areas deep in the tooth is even more increased. Experiments have shown that the known light-curable dental materials which have a minimal shrinkage during polymerization absorb a portion of the light output required for polymerization so that with increasing depth the amount of light available for polymerization decreases and thus its curing powers due to absorption of the UV portion of the light. This effect cannot be compensated by extending the polymerization period or can be compensated only unsatisfactory especially since a long polymerization time is cumbersome for the patient as well as the dentist.

It is therefore an object of the present invention to provide a light-curing device of the aforementioned kind which allows for a considerably reduced polymerization period, but, at the same time, ensures safe light curing of areas deep within the tooth. They are to be manufactured relatively inexpensively and should have improved handling.

SUMMARY OF THE INVENTION

The inventive mains-operated device for curing by light a polymerizable dental material according to the present invention is primarily characterized by a housing having a light guide and a cooling fan. A halogen light source, comprising a reflector and a spiral-mound filament, is positioned in the housing and emits light through the light guide. A control device is connected to the light source. The reflector is positioned at end of the filament remote from the light guide. The reflector is transmissive for infrared radiation and is positioned in a cooling air flow of the fan. The control device supplies the filament with a voltage to 100 V to 240 V whereby the filament provides luminance of more than 750 cd.

The filament preferably provides illuminance of more than 4,000 cd.

The control device is without transformer and has a thermistor or a triac for providing a phase-controlled increasing supply voltage upon switching on the light source.

The control device comprises a push button for alternatingly switching on and off the device.

The device is a hand-held apparatus having a pistol shape including a grip. The device also includes a cable with a plug for connecting the device to the outlet of an electric mains, wherein the cable is connected to the lower end of the grip.

The control device is enclosed in the housing and the dental material is contained in the housing. The device includes a cable with plug extending from the housing for connecting without transformer the device to an outlet of an electric mains.

The light source is preferably a high-voltage incandescent light bulb and has a plug-in contact received in a receiving socket of the housing.

The light source may be a high-voltage incandescent light bulb having a socket with an outer thread received in a receiving socket of the housing.

The filament is preferably a double coil extending in the coiled state over a length of at least 2 cm, wherein the filament is bent twice in close vicinity of the optical axis of the reflector.

The filament is preferably V-shaped when viewed in a side viewed.

The device may further comprise a cable with a plug extending from the housing and connecting without transformer the device to an outlet of the electric mains, wherein the housing consists of plastic material and has an inner wall coated with a metal coating The metal coating is connected to a ground wire of the cable.

The housing has preferably a protective coating against electric and/or electromagnetic radiation.

The protective coating consists of Mu metal.

Preferably, the housing comprises an electrically insulating material having a voltage resistance that is a multiple of the mains voltage.

The electrically insulating material is plastic and the voltage resistance is ten times the mains voltage.

Advantageously, the device has an additional insulating inner housing covering the receiving socket for the light source and voltage conducting parts of the device.

Surprisingly, the inventive light-curing device with a substantially increased light output (luminance) provides for a secure curing of areas of the dental material filling positioned deep within a cavity. Apparently, the inventively strong and very bright light radiation is reflected, especially for deep fillings, also at the dentin of the tooth whereby the reflected radiation contributes to light curing of the deep portions of the filling. Due to the more or less sudden polymerization, the damping effect of the upper portions of the dental material even for rather opaque dental materials is less pronounced so that over all the polymerization result is improved.

Even though due to the enormously fast polymerization the heat loading of the corresponding dental material is increased, the heat loading, is however, so short that no heat damage of the tooth having the filling will result because the tooth before polymerization is already at body temperature and short heat peaks can be easily dissipated.

Inventively, it is especially advantageous that the use of a control device without transformer eliminates the corresponding electromagnetic radiation so that no disruptions of other diagnostic tools can occur. When needed, a soft start via phase control by thyristor or triac can be realized. Due to the inventively longer filament of the halogen light source, even for a normal fast start of the light source, a delay of approximately a second will occur until the entire light output is available. The inventive light source thus allows for an integrated soft start without additional electronic components. It is especially favorable that the supply station, which in conventional light-curing devices must be provided in addition to the hand-held apparatus, is inventively eliminated. The only part remaining is the cable that extends preferably from the lower end of the grip of the hand-held apparatus to any mains outlet. A cable cross-section of 0.75 $mm^2$ is completely sufficient even when the light source has an electric output of 500 watt so that the cable can be embodied to be respectively flexible. A control of the light output is not needed since, due to the greatly increased output reserves, minimal mains voltage fluxuations are of no importance. The inventive light-curing device is economical to a greater extent since the control device can be reduced, when desired, to an on/off switch which in an advantageous embodiment is coupled with monitoring device for operating hours. For example, when 500 or 1,000 operating hours have been reach, the monitoring device will emit a signal as a safety means which indicates that the light source should be exchanged.

With the inventively increased light output despite the greatly reduced constructive expenditure, a substantial improvement of light curing of the dental material to be polymerized can be ensured even when the light-curing device is a stationary device that can be used for light curing of prostheses, crowns or bridges. It is especially favorable that with the elimination of the transformer, which was needed in the past, considerable costs can be saved and that the elimination of the base station furthermore reduces the required space for the device. The efficiency of the light-curing device is considerably increased, since losses that occurred conventionally within the base station, causing heating of the transformer and of the electronic control components, have been completely eliminated.

The curing of the employed light-curable dental materials depends considerably on the translucence of the material. Even for very opaque filling materials, improved curing results are observed with the inventively improved efficiency.

Preferably, the reflector of the light source is, as is known, transmissive for infrared radiation so that a great portion of the infrared radiation is guided to the rear and does not impact the dental material.

It is especially advantageous that according to one inventive embodiment the inventive light source is equipped with integrated reflector and protective glass. The bulb portion of the light source can then heat up to a temperature of 250° C. while being protected without the protective glass above the reflector becoming hot. The reflector can be aligned such that despite the long filament an excellent focusing action onto the light guide end is possible.

Preferably, the protective glass pane as well as an edge filter positioned on the light entry portion of the light guide are embodied to reflect infrared radiation. For this purpose, a double reduction of the infrared portion can be achieved which results in a further reduction of heat loading within the mouth of the patient.

According to another preferred embodiment the filament, in a manner known per se, is a twice bent double coil. Such a coil can extend with a radial deviation of maximally 3 mm relative to the optical axis in the focal point of the reflector even though a length of the filament of 4 cm is possible.

BRIEF DESCRIPTION OF THE DRAWINGS

The object and advantages of the present invention will appear more clearly from the following specification in conjunction with the accompanying drawings, in which.

DESCRIPTION OF PREFERRED EMBODIMENTS

The present invention will now be described in detail with the aid of several specific embodiments utilizing FIGS. 1 through 3.

Figure 1:
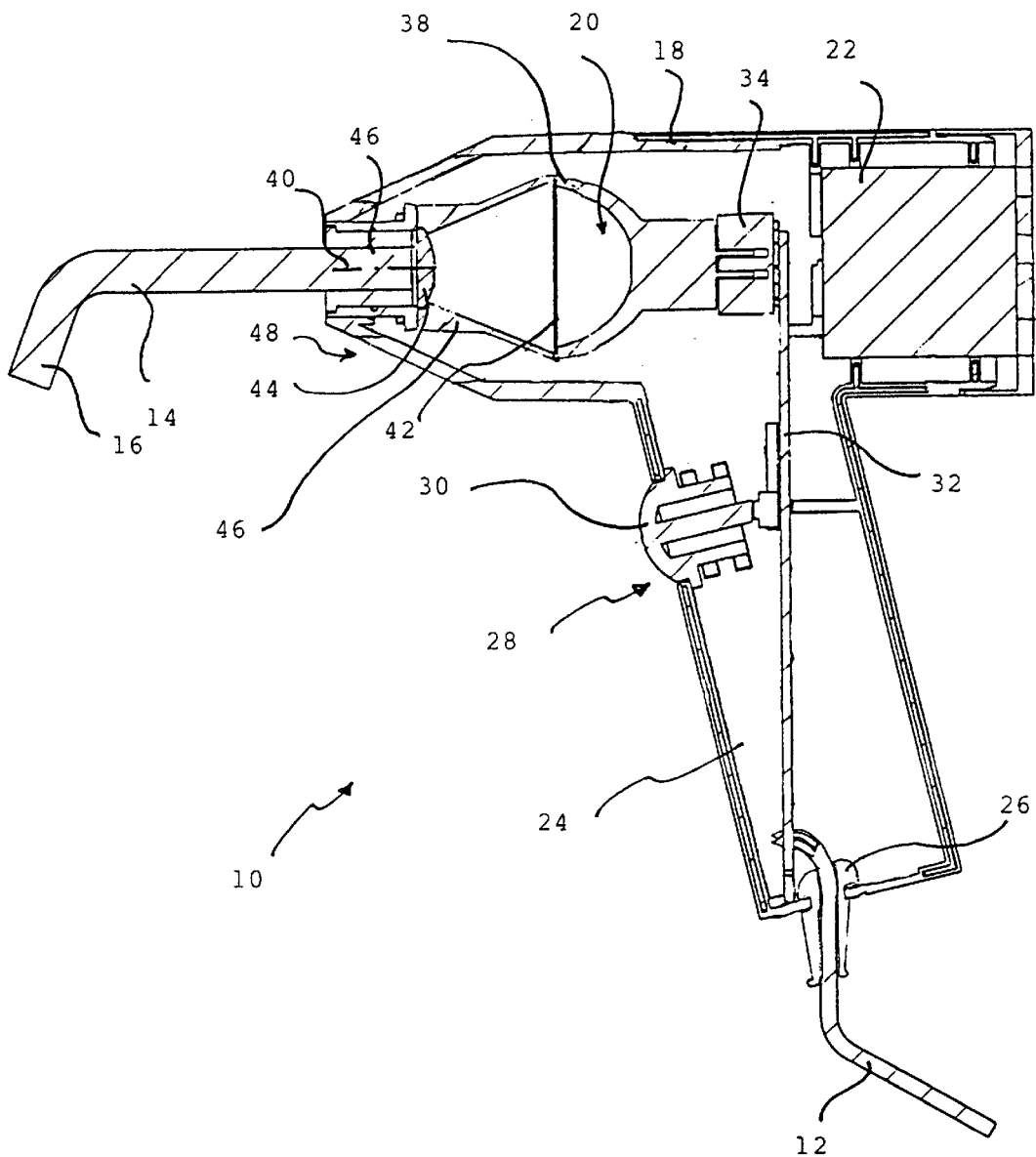
FIG. 1 shows a schematic view of an inventive light curing device.

The embodiment represented in FIG. 1 shows a hand-held light curing device 10 with a grip which has an electric cable 12 for directly connecting the device to an outlet of the mains. The inventive light curing device is substantially pistol-shaped and has at its forward end in a conventional manner a light guide 14 with bent end 16 which is designed to be introduced into the patients mouth in order to provide the light-curing action. Furthermore, the light-curing device has a housing 18 that encloses the light source 20 and a cooling fan 22 whereby the grip 24 which provides the pistol-shaped appearance of the light-curing device 10 is connected by an electric cable 12 extending from the lower end of the grip 24 to the electric mains.

The grip receives a pull protection 26 for the electric cable 12 and a control device 28 for the light-curing device. The control device 28 in the shown embodiment is limited to an on/off switch 30 which is connected to a printed circuit board 32. The printed circuit board 32 is designed such that with a corresponding embodiment with thyristors a phase control for automatically supplying a soft start can be realized. In an embodiment without soft start, this device can be bridged by a corresponding wire bridge.

The cooling fan 22 is also connected to the control device 28 and is thus switchable by the switch 30.

According to another embodiment it is suggested to connect the cooling fan 22 directly to the electric cable 12 so that the cooling fan 22 will always operate when the electric cable 12 is inserted into the non-represented outlet.

The printed circuit board 32 also has a receiving socket 34 for the light source 20. The light source 20 has a filament 36 shown in FIG. 2 and reflector 38 whereby the reflector 38, the filament 36, and the light guide 14 extend along an optical axis 40.

The light source 20 is provided with a protective glass pane 42 which is coated with a coating that reflects infrared radiation. The same holds true for the convex lens 44 which is arranged in the light entry area of the light guide 14. The space between the protective glass pane 42 and the lens 44 is sealed so as to prevent dust from entering and is surrounded by a cone member 46 which is reflectively coated in order to improve the light output.

The cooling air flow of the cooling fan is embodied so as to flow along the cone member 46 and along the reflector 38 provided with cooling ribs whereby the air outlet openings 48 are adjacent to the light entry area 46 and surround it.

Figure 2:
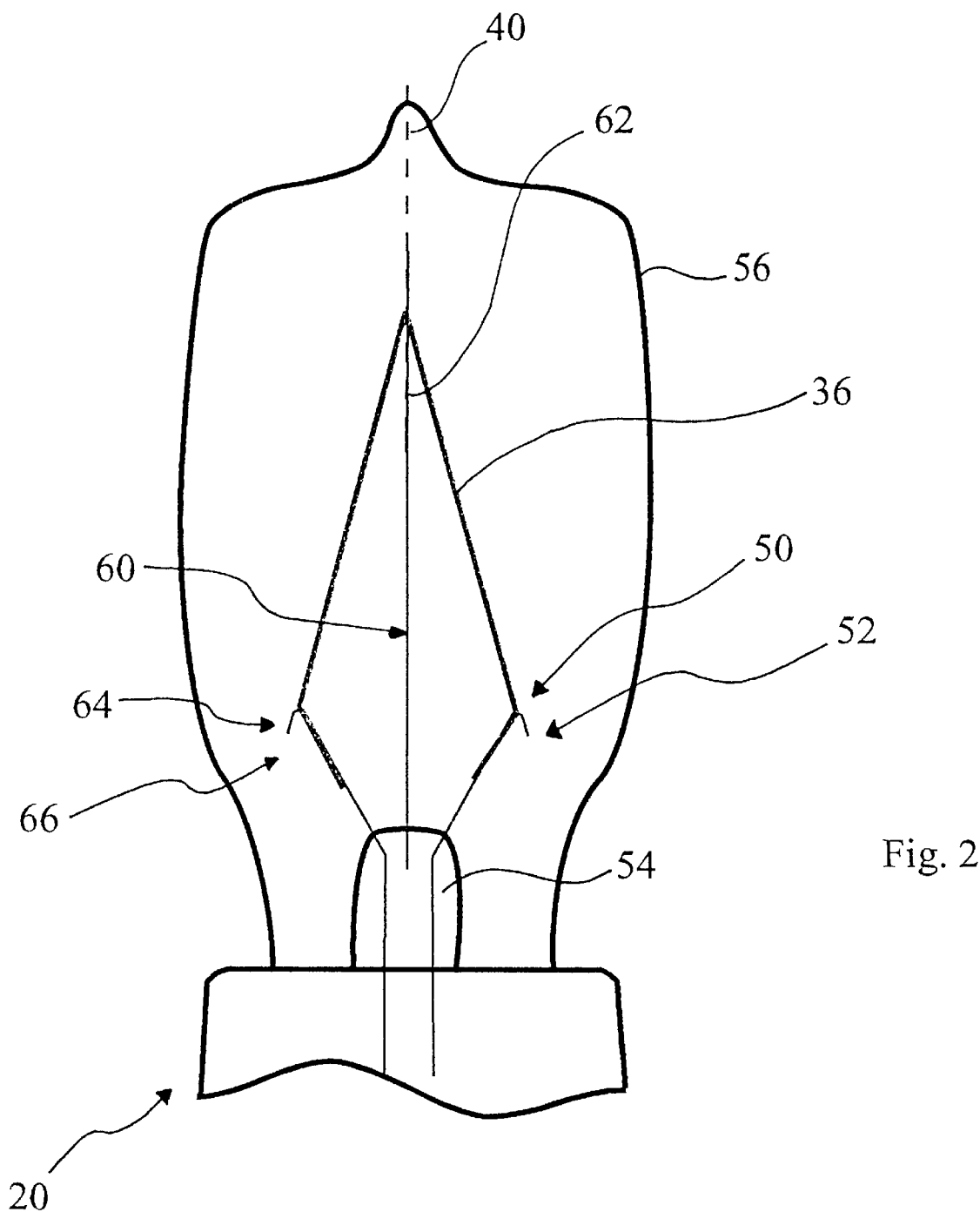
FIG. 2 shows a side view of a filament for an inventive light source for use with a light-curing device according to FIG. 1.
Figure 3:
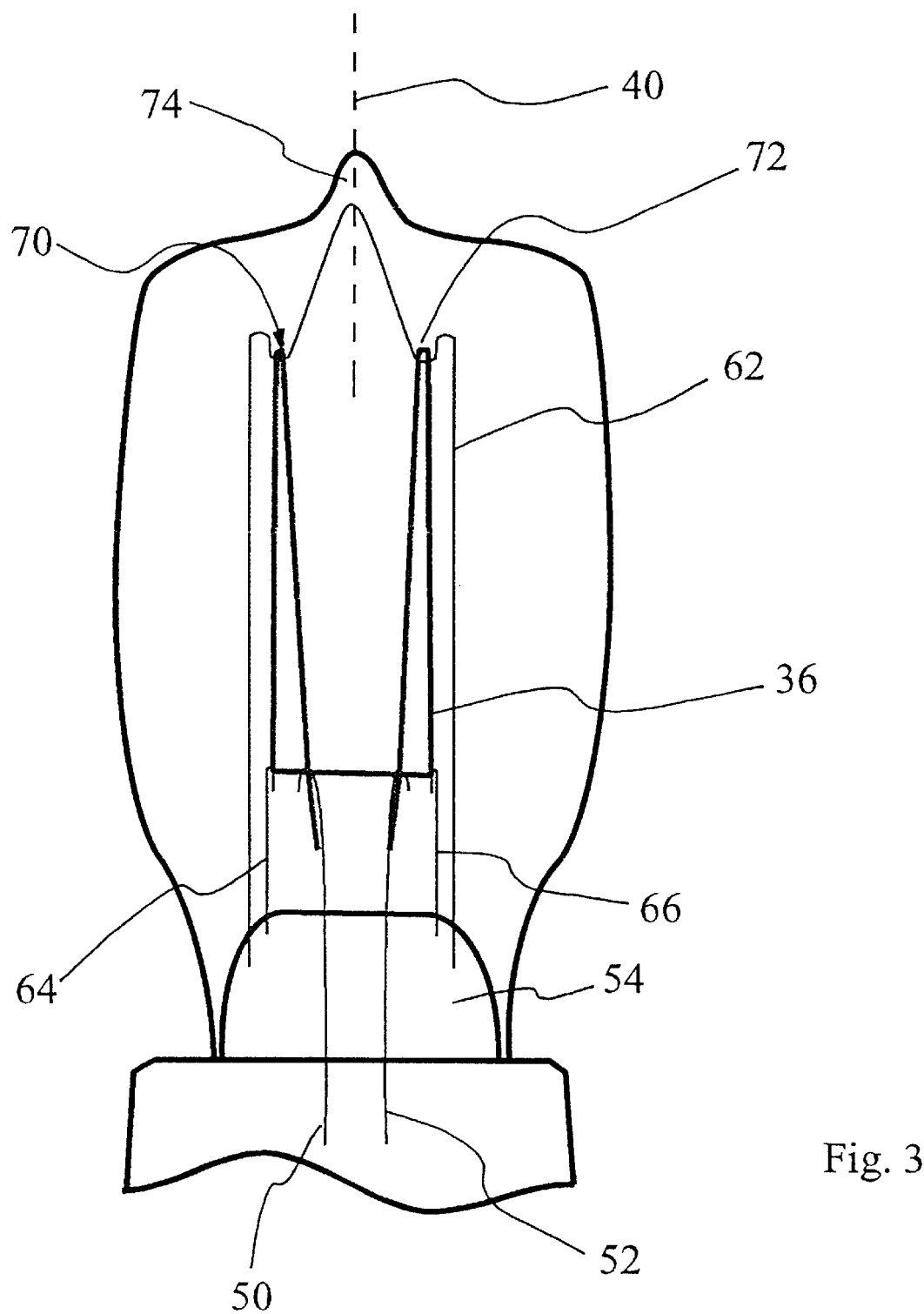
FIG. 3 shows a front view of a filament of the light source of FIG. 2.

An enlarged detail of the inventive filament is shown in FIGS. 2 and 3.

The light source 20 shown in FIG. 2 has a filament 36 which extends symmetrically to the optical axis 40 and is substantially V-shaped. It is connected to electrodes 60 and 62 which are embedded in a manner known per se in a glass socket 54. The incandescent quartz bulb 56 known from halogen lamps has a comparatively small diameter of, for example, 1 cm substantially in the longitudinal direction of the optical axis and extends over a length of approximately 2 cm.

The lamp bulb 56 is filled with a gas containing halogen, for example, bromomethane. The filament 36 is spaced at most at a distance of 3 mm from the optical axis whereby the central area 60 of the filament coincides with the focal point of the reflector. The filament 36 is guided at its forward end across 2 securing wire 62 having a design that can be seen especially well in FIG. 3. The electrodes 50, 52 have arranged oppositely thereto counter securing wires 46 embedded within the glass socket 54 which extends substantially symmetrical to the electrode 50.

As can be seen in FIG. 3, the counter securing wires 64 and 66 are laterally bent in a plan view so that, in plan view, a substantially U-shaped arrangement of the filament 36 results.

In the shown preferred embodiment the counter securing wires 64 and 66 are embedded adjacent the optical axis 40. Adjacent thereto electrodes 50 and 52 are arranged while the glass bulb 54 supports the securing wire 62 at a location relatively far to the exterior. The wire 62 is substantially extending over the entire length of the glass bulb. In the forward area, the securing wire 62 has bearing supports 70, 72 for the filament 36 and is supported at the inner side of the bulb in the vicinity of the tip 74. This design allows a relatively secure support whereby the respective free length of the filament divided into four portions of approximately 1 cm.

The filament 36 is a double coil whereby the diameter of the coil is approximately 0.05 mm and the diameter of the outer coil is approximately 0.4 mm. This coil design provides the required length of a tungsten wire to be positioned within the inventive light source with the desired stability and required resistance.

The inventive light source in the shown embodiment provides a luminance of 4,300 cd whereby it is understood that the output can vary and be adjusted in wide ranges to desired specifications.

According to a modified embodiment it is suggested to provide the housing as a plastic housing that in itself provides a protection against the mains voltage but can be additionally grounded. For this purpose the housing is completely coated with an inner metal layer, for example, by vapor deposition. The metal layer is connected to the ground wire of the three-wire mains cable.

According to a modified embodiment an additional protective housing is provided that supports the ground wire coating.

According to another embodiment a protective measure as a means against the weak electromagnetic radiation is provided. The housing in this embodiment is coated with a Mu metal whereby it is also possible to connect the Mu metal coating to the ground wire in order to provide an electrical as well as electromagnetic shielding.

The housing 18 and grip 24 of the light curing device are preferably comprised of an electrically insulating material such as plastic having a wall thickness of, for example, 5 mm. The voltage stability of the housing is a multiple of the mains voltage, for example, it is ten fold the mains voltage. The mains voltage can be the conventional voltage, whereby these values are between 100 V and 240 V. The creepage distance is preferably additionally extended.

According to a further embodiment, the light-curing device has an additional insulating inner housing that covers the receiving socket for the light source 20 and especially further voltage-carrying parts.

The aforementioned embodiments are also suitable when no ground wire is provided.

The present invention is, of course, in no way restricted to the specific disclosure of the specification and drawings, but also encompasses any modifications within the scope of the appended claims.

What is claimed is:

1. A mains-operated device for curing by light a polymerizable dental material, said device comprising:

a housing having a light guide and a cooling fan;

a halogen light source, comprising a reflector and a spiral-wound filament, positioned in said housing and emitting light through said light guide;

a control devise connected to said light source;

said reflector positioned at an end of said filament remote from said light guide;

said reflector transmissive for infrared radiation;

said reflector positioned in a cooling air flow of said fan;

said control device supplying said filament with a voltage of 100 to 240 V;

said filament providing a luminance of more than 750 cd.

2. A device according to claim 1, wherein said filament provides a luminance of more than 4000 cd.

3. A device according to claim 1, wherein said control device is without transformer and has a thyristor or a triac for providing a phase-controlled increasing supply voltage upon switching on said light source.

4. A device according to claim 1, wherein said control device comprises a push button for alternatingly switching on and off said device.

5. A device according to claim 1, wherein said device is a hand-held apparatus having a pistol shape including a grip, said device further comprising a cable with a plug for connecting said device to an outlet of an electric mains, wherein said cable is connected to a lower end of said grip.

6. A device according to claim 1, wherein said control device is enclosed in said housing and wherein a dental material is contained in said housing, said device comprising a cable with a plug extending from said housing for connecting without transformer said device to an outlet of an electric mains.

7. A device according to claim 1, wherein said light source is a high-voltage incandescent light bulb and has a plug-in contact received in a receiving socket of said housing.

8. A device according to claim 1, wherein said light source is a high-voltage incandescent light bulb having a socket with an outer thread received in a receiving socket of said housing.

9. A device according to claim 1, wherein said filament is a double coil extending in the coiled state over a length of at least 2 cm, said filament being bent twice in close vicinity of an optical axis of said reflector.

10. A device according to claim 9, wherein said filament is V-shaped in a sideview.

11. A device according to claim 1, further comprising a cable with a plug extending from said housing for connecting without transformer said device to an outlet of an electric mains, wherein said housing consists of plastic material and has an inner wall coated with a metal coating, wherein said metal coating is connected to a ground of said cable.

12. A device according to claim 1, wherein said housing has a protective coating against electric and/or electromagnetic radiation.

13. A device according to claim 12, wherein said protective coating consists of Mu-metal.

14. A device according to claim 1, wherein said housing comprises an electrically insulating material having a voltage resistance that is a multiple of the mains voltage.

15. A device according to claim 14, wherein said electrically insulating material is plastic and wherein said voltage resistance is ten times said mains voltage.

16. A device according to claim 1, wherein said device has an additional insulating inner housing covering a receiving socket for said light source and voltage conducting parts of said device.

\* \* \* \* \*